United States Patent

Miura et al.

[11] Patent Number: 4,877,907
[45] Date of Patent: Oct. 31, 1989

[54] PREPARATION PROCESS OF 4,4′-BIPHENOL, PRECURSOR OF SAME AND PREPARATION PROCESS OF PRECURSOR

[75] Inventors: Tohru Miura; Teruyuki Nagata; Koju Okazaki; Masayuki Furuya; Emiko Nishida, all of Ohmuta, Japan

[73] Assignee: Mitsui Toatsu Chemicals, Incorporated, Tokyo, Japan

[21] Appl. No.: 338,206

[22] Filed: Apr. 14, 1989

Related U.S. Application Data

[62] Division of Ser. No. 178,301, Apr. 6, 1988.

[30] Foreign Application Priority Data

Apr. 14, 1987 [JP] Japan .................................. 62-89890
Dec. 18, 1987 [JP] Japan .................................. 62-318701

[51] Int. Cl.⁴ .............................................. C07C 39/17
[52] U.S. Cl. ................................... 568/721; 568/719; 568/730; 568/743; 568/822
[58] Field of Search ............... 568/743, 730, 719, 721, 568/822

[56] References Cited

U.S. PATENT DOCUMENTS 2,368,361  1/1945  Jenkins ................................ 568/730
3,697,606  10/1972 Freudewald et al. ............... 568/730
4,723,046  2/1988  Nagata et al. ....................... 568/730

FOREIGN PATENT DOCUMENTS 0251614  6/1987  European Pat. Off. ............ 568/730
62128    4/1983  Japan .................................. 568/730

OTHER PUBLICATIONS

J. Of Organic Chemistry, 34, 1160 (1969).
Patent Abstracts of Japan, vol. 7, No. 151, (Jul. 2, 1983), (C-174), 1296.

Primary Examiner—Werren B. Lone
Attorney, Agent, or Firm—Fisher, Christen & Sabol

[57] ABSTRACT

A novel compound, 4-(4-hydroxyphenyl)-3-cyclohexene-1-ol, and a novel preparation process of 4,4′-biphenol by using the novel compound as the raw material.

4-(4-Hydroxyphenyl)-3-cyclohexene-1-ol can be obtained by conducting a thermal decomposition reaction of 4,4-bis(4-hydroxyphenyl)cyclohexanol. 4,4′-Biphenol can be industrially manufactured by conducting a dehydrogenation reaction of 4-(4-hydroxyphenyl)-3-cyclohexene-1-ol.

1 Claim, 1 Drawing Sheet

PREPARATION PROCESS OF 4,4'-BIPHENOL, PRECURSOR OF SAME AND PREPARATION PROCESS OF PRECURSOR

This is a divisional of application Ser. No. 178,301 filed Apr. 6, 1988.

BACKGROUND OF THE INVENTION a. Field of the Invention

This invention relates to a novel preparation process of 4,4'-biphenol. More particularly, it relates to a novel preparation process of 4,4'-biphenol from 4-(4-hydroxyphenyl)-3-cyclohexene-1-ol and to a novel compound 4-(4-hydroxyphenyl)-3-cyclohexene-1-ol which can be utilized as a precursor of 4,4'-biphenol.

4,4'-Biphenol is useful as a stabilizer, an intermediate of dyestuffs and a material for preparing resins such as polyesters polyepoxides, polyurethanes and polycarbonates. Much attention has particularly been focused on this compound in recent years as a material for high-temperature resistant resins.

b. Description of the Prior Art

A variety of processes have been proposed to date for the preparation of 4,4'-biphenol. 4,4'-Biphenol was first prepared by the diazo decomposition of benzidine (Chemische Berichte, 22, 335). Thereafter it was prepared by the alkali fusion of sodium 4,4'-biphenyldisulfonate [U.S. Pat. No. 2,368,361 (1942)]. In recent years, processes for obtaining biphenol by the dealkylation of tetra-tert-butyldiphenol which is derived from 2,6-di-tert-butylphenol [J. of Organic Chemistry, 34, 1160 (1969), and other sources] have been fully researched. Many patents were applied for using this process. In addition, a process by the dehalogenation and dimerization of halogenated phenols (Japanese Laid-Open Patent No. 53631/1981), and a process by the alkali treatment of dihalogenated biphenyl (Japanese Laid-Open Patent No. 22347/1979) are known. Various other processes have also been proposed these conventional processes, however, have such disadvantages as toxicity, the high cost of raw materials, problems with the disposal of waste water, severe reaction conditions and low yields.

Since the present inventors succeeded in obtaining a novel compound of 4,4-bis(4-hydroxyphenyl)cyclohexanol by the reaction of 4-hydroxycyclohexanone with phenol in the presence of a catalyst, a process for obtaining 4,4'-biphenol by the decomposition and dehydrogenation reaction of above novel compound was previously proposed (Japanese Patent Application 144734/1986). The process, however, carried out the decomposition reaction of 4,4-bis(4-hydroxyphenyl)cyclohexanol and successive dehydrogenation reaction in one step and was not always satisfactory from the industrial standpoint.

In other words, in the decomposition-dehydrogenation reaction of 4,4-bis(4-hydroxyphenyl)cyclohexanol, the generation of by-products, e.g., mainly p-phenylphenol, is inevitable and the 4,4'-biphenol usually contains more than 10% of p-phenylphenol.

Since 4,4'-biphenol has a high boiling point and a high melting point and there is few good solvents for it, it is difficult to separate by-products such as p-phenylphenol. In particular, in using 4,4'-biphenol as a monomer for polymerization, p-phenylphenol should be removed in order to prevent its action as a polymerization terminator. A remarkable amount of 4,4'-biphenol is lost during the removal of p-phenylphenol.

Therefore it is particularly necessary to inhibit the formation of p-phenylphenol as much as possible during the reaction. Conventional processes, however, are limited in the inhibition of by-products such as p-phenylphenol and have not always been satisfactory.

SUMMARY OF THE INVENTION

An object of this invention is to provide a novel process for preparing 4,4'-biphenol by way of a new reaction route.

Another object of this invention is to provide an improved process for the method described in Japanese Patent Application No. 144734/1986 in order to sharply reduce the amount of by-products. In other words, a object of this invention is to provide a novel process wherein the precursor of 4,4'-biphenol is obtained in advance by a new process and 4,4'-biphenol is prepared from the precursor, and provides a novel compound of the precursor.

The above objects are achieved by providing (1) a preparation process of 4,4'-biphenol which comprises conducting a dehydrogenation reaction of 4-(4-hydroxyphenyl)-3-cyclohexene-1-ol having the formula (I):

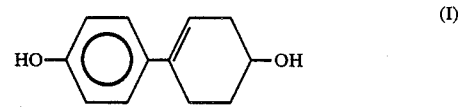

and (2) a preparation process of 4,4'-biphenol which comprises conducting a thermal decomposition reaction of 4,4-bis(4-hydroxyphenyl)cyclohexanol having the formula (II):

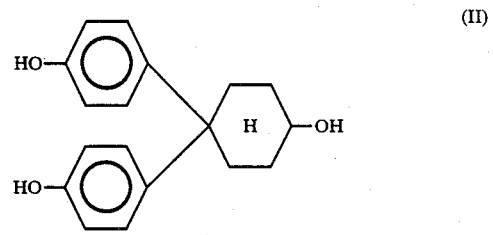

in the absence of a dehydrogenation catalyst and of a hydrogen acceptor to give 4-(4-hydroxyphenyl)-3-cyclohexene-1-ol having the formula (I):

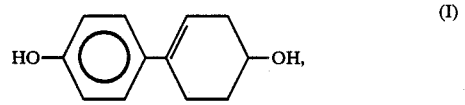

followed by conducting a dehydrogenation reaction of the compound having the formula (I). At the same time, a novel compound having the formula (I) is provided.

DETAILED DESCRIPTION OF THE INVENTION

Figure 1:
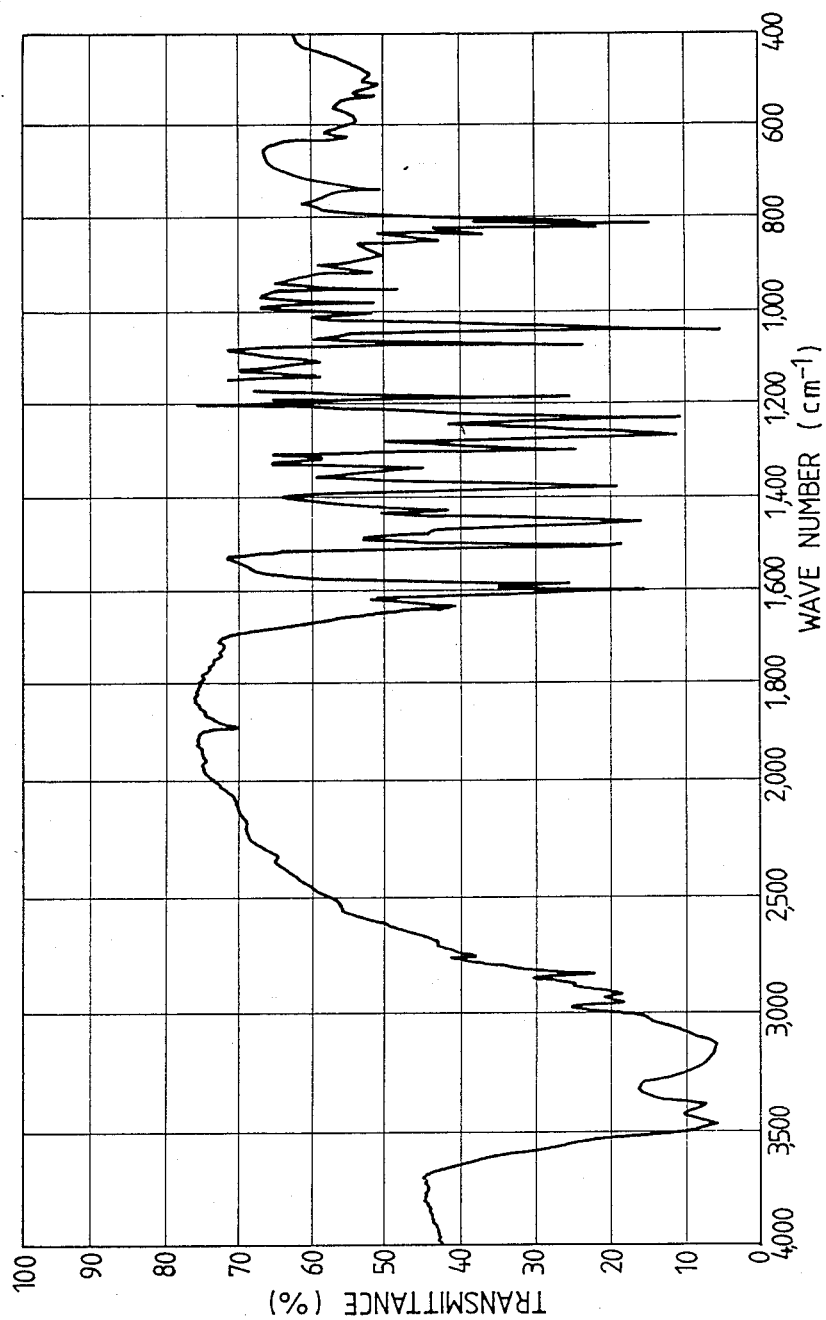
FIG. 1 illustrates an IR absorption spectrum of 4-(4-hydroxyphenyl)-3-cyclohexene-1-ol obtained in Example 2 of this invention.

The present inventors conducted further extensive research into the process which was previously proposed in Japanese Patent Application No. 144734/1986 described above. As a result, the following results were obtained:

It was found that a novel compound 4-(4-hydroxyphenyl)-3-cyclohexene-1ol can be obtained in good yield by conducting a decomposition reaction in the initial stage of a reaction in the absence of a dehydrogenation catalyst and a hydrogen acceptor, and that by-products such as p-phenylphenol can be virtually inhibited by conducting the dehydrogenation reaction of the novel compound to give 4,4'-biphenol of high purity.

In the preparation process of 4,4'-biphenol in this invention, 4,4'-biphenol is obtained from 4-(4-hydroxyphenyl)-3-cyclohexene-1-ol, the compound having the formula (I). In addition, in the case of using 4,4-bis(4-hydroxyphenyl)cyclohexanol, the compound having the formula (II) is used as the starting material, the precursor compound having the formula (I) is formed by conducting the decomposition reaction of said cycloxanol, follow by, the desired product is obtained by conducting the dehydrogenation reaction of the precursor. In other words, the dehydrogenation reaction is carried out in a separate step from the decomposition reaction.

Compared with the process described above in Japanese Patent Application No. 144734/1986 wherein the desired product is obtained in one step from the compound having the formula (I), the process of this invention allows the reaction to proceed under mild conditions, sharply inhibits the formation of by-products such as p-phenylphenol and also enhances the yield.

4-(4-Hydroxyphenyl)-3-cyclohexene-1-ol of the formula (I), which can be employed as the starting material or precursor of this invention, is a novel compound and can be obtained by conducting the thermal decomposition reaction of 4,4-bis(4-hydroxyphenyl)cyclohexanol having the formula (II).

In addition, 4,4-bis(4-hydroxyphenyl)cyclohexanol of the formula (II) can be obtained by the condensation reaction of 4-hydroxycyclohexanone with phenol, and the inventors have already applied for a patent on this compound (Japanese Patent Application No. 185221/1986).

A basic or acidic catalyst is used in the thermal decomposition reaction of the compound having the formula (II) in this invention. Effective basic catalysts which may be used for the decomposition include, for example, alkali metal hydroxides such as sodium hydroxide, potassium hydroxide and lithium hydroxide; alkali earth metal hydroxides such as magnesium hydroxide and barium hydroxide; carbonates; acetates; phenoxides; and salts of weak organic acids.

In addition, acidic catalysts which may be used include, for example, acids such as p-toluenesulfonic acid, weakly acidic acid salts such as potassium hydrogen sulfite, aluminum chloride, stannous chloride and other acidic metal chlorides.

Strongly basic catalysts such as sodium hydroxide are preferred among these catalysts.

The amount of catalyst used is normally in the range of 0.01–20%, preferably in the range of 0.1–15% per hundred parts by weight of 4,4-bis(4-hydroxyphenyl)cyclohexanol and its adducts.

The decomposition reaction may be carried out in the range of 100°–400° C., preferably in the range of 150°–250° C. When the reaction temperature is below this range, the reaction rate is too low. On the other hand, a reaction temperature above this range is unfavorable because of side reactions.

The decomposition reaction may also be carried out in a vapor phase. The vapor phase reaction, however, must be carried out at high temperatures above 300° C. due to the high melting points of the raw material and products. The reaction is preferably carried out in a liquid phase in view of yields, ease of operation, energy saving and other factors. The reaction is preferably conducted in the presence of a solvent. Examples of solvents which may be used include water; ethers such as ethylene glycol monomethyl ether, ethylene glycol dimethyl ether, diethylene glycol monomethyl ether, tetrahydrofuran, dioxane, dipropyl ether and diphenyl ether; alcohols such as ethanol, isopropyl alcohol, butyl alcohol, octyl alcohol, 2-ethylhexanol, ethylene glycol, diethylene glycol, triethylene glycol and propylene glycol; nitriles such as acetonitrile, propionitrile and benzonitrile; aromatic hydrocarbons such as benzene, toluene, xylene, mesitylene, ethylbenzene and cumene; and polar organic solvents such as 1,3-dimethyl-2-imidazolidinone, N-methylpyrrolidone, dimethylformamide, dimethyl sulfoxide and dimethylacetamide.

The decomposition reaction is an equilibrium reaction. When phenol formed is taken out of the reaction system during the reaction process, it is possible to obtain substantially 100% conversion of the raw material, 4,4-bis(4-hydroxyphenyl)cyclohexanol.

In the above method of Japanese Patent Application No. 144734/1986, 4,4'-biphenol can be obtained in one step from the raw material by conducting the decomposition reaction of 4,4-bis(4-hydroxyphenyl)cyclohexanol in the presence of a dehydrogenation catalyst and a hydrogen acceptor. On the other hand, the preparation process of this invention must be carried out in the absence of a dehydrogenation catalyst and of a hydrogen acceptor.

Since the reaction product, 4-(4-hydroxydiphenyl)-3-cyclohexene-1-ol, can be easily separated from the raw material, 4,4-bis(4-hydroxyphenyl)cyclohexanol, the reaction may also be carried out in a closed system, and unreacted 4,4-bis(4-hydroxyphenyl)cyclohexanol may be separated, recovered and reused.

After the decomposition reaction, the resulting 4-(4-hydroxyphenyl)-3-cyclohexene-1-ol is separated from solvents and low-temperature boiling impurities such as phenol, and purified by a method such as crystallization, as required.

4,4-Bis(4-hydroxyphenyl)cyclohexanol, the compound of formula (II), is largely or completely obtained in the form of phenol adducts in the preparation step, and also provides stable adducts with alcohols, water, in the separation and purification steps. These adducts may be used as is in the decomposition reaction of this invention.

These adducts, of course, can be easily dissociated by heating in a solvent such as benzene, toluene or xylene, since the solvent does not form adducts and is not reactive with the compound having the formula (I) in this invention. The decomposition reaction may be conducted after the dissociation.

The dehydrogenation reaction in the process of this invention is normally carried out in the presence of a catalyst.

Any known dehydrogenation catalyst may be used. Examples of such catalysts include nickel catalysts wherein Raney nickel, reduced nickel or nickel is supported on various carriers such as diatomaceous earth, alumina, pumice, silica gel and acid clay; cobalt catalysts such as Raney cobalt, reduced cobalt and cobalt-carrier catalyst; copper catalysts such as Raney copper, reduced copper and copper-carrier catalyst; palladium catalysts such as palladium black, palladium oxide, colloidal palladium, palladium carbon, palladium-barium sulfate, palladium-magnesium oxide, palladium calcium oxide and palladium-alumina; platinum catalysts such as platinum black, colloidal platinum, platinum oxide and platinum sulfide; and platinum-carrier catalysts such as platinum-carbon; rhodium catalysts such as colloidal rhodium rhodium-carbon and rhodium oxide; platinum group catalysts such as ruthenium catalysts; rhenium catalysts such as dirhenium heptoxide and rhenium-carbon; copper chrome oxide catalysts; molybdenum oxide catalysts; vanadium oxide catalysts; tungsten oxide catalysts; and silver catalysts.

Platinum group catalysts such as palladium catalyst are preferred among these catalysts. The amount of the dehydrogenation catalyst used is normally in the range of 0.001–0.2 gram atom, and preferably in the range of 0.004–0.1 gram atom as metal atom of the above dehydrogenation catalyst per mole of 4-(4-hydroxyphenyl)-3-cyclohexene-1-ol.

Although the dehydrogenation reaction can be carried out in the absence of a hydrogen acceptor, a higher yield can be obtained with a hydrogen acceptor.

Any type of hydrogen acceptor may be used in this invention. Several types of compounds which may be used as the hydrogen acceptor include, for example, ethylenically unsaturated organic compounds such as ethylene and propylene; acetylenically unsaturated organic compounds such as acetylene and methylacetylene; azo-containing organic compounds such as azobenzene; nitro compounds; carboxyl compounds; and phenol compound.

The preferred hydrogen acceptor is an organic compound containing conjugated double bonds and includes styrenes such as α-methylstyrene, nitrobenzene, maleic anhydride, methylacetylene, crotonic acid and phenol. The hydrogen acceptor must be highly active and should also be selected so as to obtain a useful compound by the hydrogenation of the acceptor, for example, cumene from α-methylstyrene and cyclohexanone from phenol.

The reaction temperature is generally in the range of 100°–300° C., and preferably in the range of 150°–200° C. The reaction may be carried out at relatively low temperatures. A slow reaction rate results from reaction temperatures below this range whereas unfavorable side reactions are caused by reaction temperatures above this range.

The dehydrogenation reaction may also be carried out in a vapor phase. The vapor phase reaction, however, must be conducted at high temperatures above 300° C. due to the high melting points of the raw material and products. The reaction is preferably conducted in a liquid phase in view of the yield, ease of operation and energy saving. The dehydrogenation reaction in the liquid phase is preferably carried out in the presence of a solvent. Examples of solvents which may be used include water; ethers such as ethylene glycol monomethyl ether, ethylene glycol dimethyl ether, diethylene glycol monomethyl ether, tetrahydrofuran, dioxane, dipropyl ether and diphenyl ether; alcohols such as ethanol, isopropyl alcohol, propyl alcohol, butyl alcohol, octyl alcohol, 2-ethylhexanol, ethylene glycol, diethylene glycol, triethylene glycol and propylene glycol; nitriles such as acetonitrile, propionitrile and benzonitrile; and aromatic hydrocarbons such as benzene, toluene, xylene, mesitylene, ethylbenzene and cumene. Further, the above hydrogen acceptor may also be used as the solvent.

The resulting 4,4'-biphenol in the process of this invention may be isolated by removing the catalyst from the reaction mixture after completing the reaction, followed by conducting such procedures as crystallization.

EXAMPLE 1

A four-necked glass flask was charged with 56.9 g (0.20 mole) of 4,4-bis(4-hydroxyphenyl)cyclohexanol, 5.7 g of sodium hydroxide and 100 ml of 1,3-dimethyl-2-imidazolidinone. The mixture was reacted in a nitrogen atmosphere with stirring at 190° C. for 3 hours. After cooling, the reaction mixture was neutralized to pH 7 with an aqueous hydrochloric acid solution. Then 1,3-dimethyl-2-imidazolidinone and phenol formed were distilled off under reduced pressure. The residual mass was recrystallized from isopropanol. In conducting the recrystallization, insoluble matter during the reflux which was mainly composed of inorganic salts was removed by hot filtering and the filtrate was cooled. 4-(4-Hydroxyphenyl)-3-cyclohexene-1-ol was obtained as a wet cake.

In the next step, a stainless steel autoclave was charged with the total amount of the above wet cake, 0.35 g of 5% palladium-carbon, 5.9 g of α-methylstyrene and 100 ml of 2-ethylhexanol and the internal atmosphere was replaced with nitrogen gas. The mixture was reacted at 180° C. for 3 hours, then cooled to 150° C. and filtered to recover the insoluble catalyst. 2-Ethylhexanol, α-methylstyrene and cumene formed by the reaction were distilled off from the filtrate under reduced pressure to obtain 33.6 g of 4,4'-biphenol as white crystals. The product had a purity of 98.2% based on liquid chromatography and contained 1.2% of p-phenylphenol as impurities. The yield of 4,4'-biphenol converted to a purity basis was 89% based on 4,4-bis(4-hydroxyphenyl)cyclohexanol.

COMPARATIVE EXAMPLE 2

A 300-ml stainless steel autoclave was charged with 17.1 g (0.060 mole) of 4,4-bis(4-hydroxyphenyl)cyclohexanol, 2.6 g (0.065 mole) of sodium hydroxide, 21.3 g (0.18 mole) of α-methylstyrene, 100 g of water and 0.2 g of 5% palladium-carbon, and the internal atmosphere was replaced with nitrogen gas. The mixture was reacted at 250° C. for 4 hours. The reaction mixture was cooled after completing the reaction. The partly separated crystals were dissolved by adding 30.0 g of 20%-aqueous sodium hydroxide solution. The catalyst was removed by filtering the resulting mixture. α-Methylstyrene and cumene were extracted with 100 ml of benzene from the filtrate. An aqueous hydrochloric acid solution was added to the residual filtrate to precipitate the desired product. The separated crystals were filtered, washed with water and dried to obtain 10.8 g of crystals. The product had a purity of 85.8% based on liquid chromatography and contained 11.0% of p-phenylphenol as impurities. The yield of 4,4'-biphenol converted to a purity basis was 83%.

EXAMPLE 2

The decomposition reaction and recrystallization were carried out with the same procedures as in Example 1. The resulting wet cake of 4-(4-hydroxyphenyl)-3-cyclohexene-1-ol was dried to obtain 35.0 g of white crystals.

The pure product obtained by recrystallizing twice from acetonitrile had a melting point of 194° C. Table 1 illustrates the results of $^1$H-NMR and FIG. 1 shows an IR absorption spectrum (KBr tablet method), respectively, of the pure product.

TABLE 1

| Signal | δ (p.p.m.) | Proton ratio | Assignment |
|---|---|---|---|
| a | 1.4–2.4 | 6 | $CH_2 \times 3$ |
| b | 3.7 | 1 | CH |
| c | 4.1–4.4 | 1 | OH |
| d | 5.7–5.9 | 1 | CH |
| e | 6.6–6.8 | 2 | p-substituted benzene |
| f | 7.0–7.2 | 2 | |
| g | 8.8–9.0 | 1 | OH |

Measuring conditions: Solvent DMSO-D$_6$, Temperature 80° C.

```
         (d)
          H
    (e) (f)    (a)
              \   OH (c)
(g) HO—⟨  ⟩—⟨  ⟩
              /   H (b)
    (e) (f)  (a) (a)
```

EXAMPLE 3

The same reaction and post-treatment as described in Example 1 were carried out, except that 75.7 g (0.20 mole) of the phenol adduct of 4,4-bis(4-hydroxyphenyl)cyclohexanol was used in place of 56.9 g (0.20 mole) of 4,4-bis(4-hydroxyphenyl)cyclohexanol. 4,4'-Biphenol was obtained as white crystals in a yield of 33.8 g. The product had a purity of 98.1% based on liquid chromatography and a p-phenylphenol content of 1.2%.

EXAMPLE 4

A 300-ml stainless steel autoclave was charged with 38.0 g (0.20 mole) of 4-(4-hydroxyphenyl)-3-cyclohexene-1-ol, 1.5 g of 5% palladium-carbon, 70.9 g (0.60 mole) of α-methylstyrene and 100 g of water, and the internal atmosphere was replaced with nitrogen. The mixture was heated and reacted at 200° C. for 3 hours. The reaction mass was poured into a large volume of an aqueous sodium hydroxide solution, and the insoluble catalyst was removed by filtration. The organic layer was removed from the filtrate. The rest of the filtrate was neutralized to pH 4 by adding an aqueous hydrochloric acid solution. The separated crystals were filtered, washed with water and dried to obtain 37.0 g of 4,4'-biphenol as white crystals. The product had a purity of 98.0% and the yield was 97.4% based on 4-(4-hydroxyphenyl)-3-cyclohexene-1-ol.

EXAMPLE 5

A 300-ml four-necked glass flask was charged with 38.0 g (0.20 mole) of 4-(4-hydroxyphenyl)-3-cyclohexene-1-ol, 0.4 g of 5% palladium carbon, 59.1 g (0.50 mole) of o-methylstyrene and 100 ml of 2-ethylhexanol. The mixture was reacted at 160° C. for 4 hours in a nitrogen atmosphere. The reaction mixture was hot filtered at 150° C. to recover the palladium-carbon. 2-Ethylhexanol, α-methylstyrene and cumene formed were distilled off from the filtrate under reduced pressure. 37.2 g of white crystals of 4,4'-biphenol were obtained. The product had a purity of 98.6% based on liquid chromatography, a p-phenylphenol content of 0.9% and a yield converted to a purity basis of 98.5%.

High purity 4,4'-biphenol useful as the raw material of high-temperature resistant resins and other intermediates can be obtained in high yield according to this invention.

We claim:

1. A preparation process of 4-(4-hydroxyphenyl)-3-cyclohexene-1-ol which comprises conducting a thermal decomposition reaction of 4,4-bis(4-hydroxyphenyl)cyclohexanol having the formula (II):

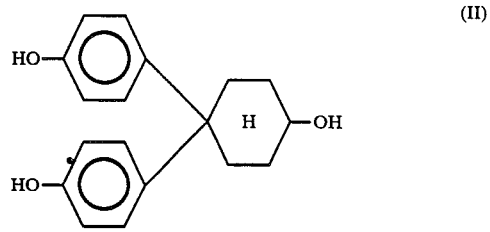

(II)

in the absence of a dehydrogenation catalyst and of a hydrogen acceptor.

* * * * *